US009463445B2

(12) United States Patent
Barton et al.

(10) Patent No.: US 9,463,445 B2
(45) Date of Patent: *Oct. 11, 2016

(54) CATALYSTS AND METHODS FOR ALCOHOL DEHYDRATION

(71) Applicant: Dow Global Technologies LLC, Midland, MI (US)

(72) Inventors: David G. Barton, Midland, MI (US); Adam Chojecki, Ghent (BE); Paul R. Elowe, Midland, MI (US); Beata A. Kilos, Midland, MI (US); Adam S. Cieszlak, Bay City, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/764,370

(22) PCT Filed: Mar. 13, 2014

(86) PCT No.: PCT/US2014/025232
§ 371 (c)(1),
(2) Date: Jul. 29, 2015

(87) PCT Pub. No.: WO2014/151220
PCT Pub. Date: Sep. 25, 2014

(65) Prior Publication Data
US 2015/0375214 A1    Dec. 31, 2015

Related U.S. Application Data

(60) Provisional application No. 61/803,891, filed on Mar. 21, 2013.

(51) Int. Cl.
| | | |
|---|---|---|
| *C07C 41/09* | (2006.01) |
| *C09K 5/00* | (2006.01) |
| *B01J 27/125* | (2006.01) |
| *B01J 37/08* | (2006.01) |
| *B01J 37/22* | (2006.01) |
| *B01J 37/24* | (2006.01) |
| *B01J 23/10* | (2006.01) |
| *C09K 5/10* | (2006.01) |
| *B01J 37/03* | (2006.01) |
| *B01J 27/10* | (2006.01) |
| *B01J 35/00* | (2006.01) |
| *B01J 35/10* | (2006.01) |
| *B01J 27/06* | (2006.01) |
| *C09K 5/06* | (2006.01) |

(52) U.S. Cl.
CPC .............. *B01J 27/125* (2013.01); *B01J 23/10* (2013.01); *B01J 27/06* (2013.01); *B01J 27/10* (2013.01); *B01J 35/002* (2013.01); *B01J 35/1009* (2013.01); *B01J 35/1038* (2013.01); *B01J 37/031* (2013.01); *B01J 37/088* (2013.01); *B01J 37/22* (2013.01); *B01J 37/24* (2013.01); *C07C 41/09* (2013.01); *C09K 5/063* (2013.01); *C09K 5/10* (2013.01)

(58) Field of Classification Search
CPC ................................. C07C 41/09; C09K 5/10
USPC .................................... 568/635, 645; 252/73
See application file for complete search history.

(56) References Cited

U.S. PATENT DOCUMENTS

| | | | |
|---|---|---|---|
| 1,873,537 | A | 8/1932 | Brown et al. |
| 4,013,694 | A | 3/1977 | Fishel |
| 4,156,698 | A | 5/1979 | Dwyer et al. |
| 4,898,982 | A | 2/1990 | Hussmann |
| 5,144,094 | A | 9/1992 | Richmond |
| 5,288,922 | A | 2/1994 | Buske |
| 5,925,798 | A | 7/1999 | Gambell et al. |
| 8,460,626 | B2 | 6/2013 | Larcher et al. |
| 8,728,435 | B2 | 5/2014 | Larcher et al. |
| 8,907,136 | B2 | 12/2014 | Elowe et al. |
| 9,051,252 | B2 | 6/2015 | Barton et al. |

(Continued)

FOREIGN PATENT DOCUMENTS

| | | |
|---|---|---|
| GB | 649999 | 2/1951 |
| JP | H0285224 | 3/1990 |

(Continued)

OTHER PUBLICATIONS

Norman A Fishel et al: "O-Phenylphenol from Phenol: A two-step selective substitution process", Catalysis in Organic Syntheses: Proceedings of the 7. Conference on Catalysis in Organic Syntheses, Held in Chicago, Jun. 5-7, 1978, Acad. Press, US, Jan. 1, 1980, pp. 119-132.

Chemistry International—Newsmagazine for IUPAC, Chinese Terms for Chemical Elements, Chang Hao, IUPAC publications, 2004, pp. 1-6.

Nomenclature of Inorganic Chemistry, IUPAC Recommendations 2005, RSC Publishing 2005, pp. 1-377.

Cotton, "Scandium, Yttrium and the Lanthanides: Inorganic and Coordination Chemistry", Encyclopedia of Inorganic Chemistry, published online Mar. 15, 2006, pp. 1-40.

(Continued)

*Primary Examiner* — Sikarl Witherspoon
(74) *Attorney, Agent, or Firm* — Joe R. Prieto; KSJLAW, LLC

(57) ABSTRACT

Provided is a process for preparing a diaryl ether compound through the dehydration of an aromatic alcohol compound in the presence of a halogenated rare earth element oxide catalyst, providing a reaction vessel having loaded therein a rare earth element oxide; halogenating the rare earth element oxide with a halogen source to form an activated catalyst; and dehydrating an aromatic alcohol compound over the activated catalyst to form the diaryl ether compound, where the halogenating and dehydrating steps occur in the same vessel. The rare earth element oxide is an oxide of a light rare earth element, an oxide of a medium rare earth element, an oxide of a heavy rare earth element, an oxide of yttrium, or a mixture of two or more thereof.

7 Claims, No Drawings

(56) References Cited

U.S. PATENT DOCUMENTS

| | | |
|---|---|---|
| 9,150,479 B1 | 10/2015 | Barton et al. |
| 2006/0210462 A1 | 9/2006 | Larcher et al. |
| 2015/0190790 A1 | 7/2015 | Barton et al. |
| 2015/0191638 A1 | 7/2015 | Barton et al. |
| 2015/0375214 A1 | 12/2015 | Barton et al. |

FOREIGN PATENT DOCUMENTS

| | | |
|---|---|---|
| WO | 02060818 | 8/2002 |
| WO | 2013095850 | 6/2013 |
| WO | 2013181237 | 12/2013 |
| WO | 2013181238 | 12/2013 |
| WO | 2014204684 | 12/2014 |

OTHER PUBLICATIONS

Fishel, et al., "O-Phenylphenol from Phenol: A Two-Step Selective Substitution Process", Catalysis in Organic Syntheses: Proceedings of the 7th Conference on Catalysis in Organic Syntheses, Held in Chicago, Jun. 5-7, 1978, Acad. Press, US, Jan. 1, 1980, pp. 119-132.

Jiao, et al., Catalytic Synthesis of Dioctyl Phthalate from Rare Earth Oxide, Rare Earth, No. 4, Dec. 31, 1986, 52-55.

CATALYSTS AND METHODS FOR ALCOHOL DEHYDRATION

FIELD

This invention relates generally to catalysts and methods for the dehydration of aromatic alcohol compounds to ethers. More particularly, the invention uses a halogenated rare earth element oxide catalyst for the dehydration of aromatic alcohol compounds to diaryl ethers.

BACKGROUND

Diaryl ethers are an important class of industrial materials. Diphenyl oxide (DPO), for instance, has many uses, most notably as the major component of the eutectic mixture of DPO and biphenyl, which is the standard heat transfer fluid for the concentrating solar power (CSP) industry. With the current boom in CSP has come a tightening of the supply of DPO globally and questions surrounding the sustainability of the technology have arisen.

Diaryl ethers are currently manufactured commercially via two major routes: reaction of a haloaryl compound with an aryl alcohol; or gas-phase dehydration of an aryl alcohol. The first route, for example where chlorobenzene reacts with phenol in the presence of caustic and a copper catalyst, typically leads to less pure product and requires high pressure (5000 psig), uses an expensive alloy reactor and produces stoichiometric quantities of sodium chloride.

The second route, which is a more desirable approach, accounts for the largest volume of diaryl ethers produced but requires a very active and selective catalytic material. For instance, DPO can be manufactured by the gas-phase dehydration of phenol over a thorium oxide (thoria) catalyst (e.g., U.S. Pat. No. 5,925,798). A major drawback of thoria however is its radioactive nature, which makes its handling difficult and potentially costly. Furthermore, the supply of thoria globally has been largely unavailable in recent years putting at risk existing DPO manufacturers utilizing this technology. Additionally, other catalysts for the gas-phase dehydration of phenol, such as zeolite catalysts, titanium oxide, zirconium oxide and tungsten oxide, generally suffer from lower activity, significantly higher impurity content and fast catalyst deactivation.

With a chronic shortage of diaryl ethers such as DPO in sight and a pressing need to increase capacity, it has become crucial to develop alternate methods to produce such materials in a cost-effective and sustainable manner.

The problem addressed by this invention, therefore, is the provision of new catalysts and methods for manufacture of diaryl ethers from aryl alcohol compounds.

STATEMENT OF INVENTION

We have found that halogenated rare earth oxide-based materials are effective catalysts for the preparation of diaryl ethers from aromatic alcohol compounds. Advantageously, the catalysts exhibit remarkable selectivity for the desired product. Moreover, in some embodiments, the invention enables the in situ generation of the catalyst, such that catalysts may be conveniently obtained in a reactor vessel directly rather than separately prepared and then loaded into the reactor. The activation step includes feeding a source of halogen atoms, preferably chlorine, to an otherwise less active rare earth oxide-based material to generate a highly active and selective catalyst for alcohol dehydration.

In one aspect, therefore, there is provided a method for preparing a diaryl ether compound, the method comprising: providing a reaction vessel having loaded therein a rare earth element oxide; halogenating the rare earth element oxide with a halogen source to form an activated catalyst; and dehydrating an aromatic alcohol compound over the activated catalyst to form the diaryl ether compound, where the halogenating and dehydrating steps occur in the same vessel.

In another aspect, there is provided a method for producing a heat transfer fluid, the method comprising:
(a) preparing a diaryl ether compound by
  (i) providing a reaction vessel having loaded therein a rare earth element oxide;
  (ii) halogenating the rare earth element oxide with a halogen source to form an activated catalyst; and
  (iii) dehydrating an aromatic alcohol compound over the activated catalyst to form the diaryl ether compound;
(b) isolating the diaryl ether from the activated catalyst; and
(c) mixing the isolated diaryl ether compound with biphenyl such that a eutectic mixture is formed.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, the invention provides methods for producing a diaryl ether compound by dehydrating an aromatic alcohol compound in the presence of an activated catalyst. In some embodiments, the activated catalyst may be conveniently obtained directly in a reactor vessel through in situ generation. The activation step includes feeding a source of halogen atoms to a rare earth element oxide-based material to generate a halogenated rare earth element oxide-based material, which is the activated catalyst.

It has been discovered that activated catalysts as described herein exhibit high selectivity for the desired diaryl ether compounds with relatively low formation of undesirable byproducts. For instance, as demonstrated by the examples, in the synthesis of diphenyl oxide from phenol, a selectivity for the DPO of 50% or greater may be achieved. In some embodiments, a selectivity of 80% or greater may be achieved. In some embodiments, a selectivity of 90% or greater, or 95% or greater is possible.

In addition to being highly selective, the catalysts are also advantageous because they are non-radioactive, thus eliminating the safety and environmental issues, as well as higher costs, associated with the handling of radioactive materials, such as the thoria catalysts of the prior art.

The method of the invention comprises: providing a reaction vessel having loaded therein a rare earth element oxide; halogenating the rare earth element oxide with a halogen source to form an activated catalyst; and dehydrating an aromatic alcohol compound over the activated catalyst to form the diaryl ether compound.

The reaction vessel may be any vessel suitable for the reaction steps as described herein and can be, for instance, a batch, semi-batch, plug-flow, continuous-flow, continuous stir type of reactor. The reaction vessel typically is configured so as to enable: control and measurement of temperature, pressure; introduction of ingredients separately or as a mixture; purging thereof by an inert gas (e.g., nitrogen gas); or charging with a reactant gas. When desired, egress of gas therefrom (e.g., excess reaction gas); introduction of the ingredients as a liquid, solid, or slurry; and, in a stirred reactor, rapid stirring of reactor contents via a stir shaft and impeller.

A preferred reactor for use in the invention is a vessel loaded with catalyst particles where gaseous reactants are fed into the vessel and flow through the catalyst bed and exit as reaction products. The halogenation may also be done using a gas phase halogenating compound or by passing a liquid stream containing a halogen compound through the catalyst bed.

According to the inventive method, a reaction vessel is provided having loaded therein a rare earth element oxide. The rare earth element oxide may be an oxide of a light rare earth element, an oxide of a medium rare earth element, an oxide of a heavy rare earth element, an oxide of yttrium, or mixtures of two or more thereof.

By a "light rare earth element" is meant lanthanum, praseodymium, neodymium, or mixtures of two or more thereof. By "oxide of a light rare earth element" is meant a compound that contains at least one oxygen-light rare earth element chemical bond. Examples include lanthanum oxide ($La_2O_3$), praseodymium oxide (e.g., $PrO_2$, $Pr_2O_3$, $Pr_6O_{11}$, or mixtures), and neodymium oxide ($Nd_2O_3$).

By a "medium rare earth element" is meant samarium, europium, gadolinium, or mixtures thereof. By "oxide of medium rare earth element" is meant a compound that contains at least one oxygen-medium rare earth element bond. Examples include $Sm_2O_3$, $Eu_2O_3$, and $Gd_2O_3$.

By a "heavy rare earth element" is meant terbium, dysprosium, holmium, erbium, thulium, ytterbium, lutetium, or mixtures thereof. By "oxide of heavy rare earth element" is meant a compound that contains at least one oxygen-heavy rare earth element bond. Examples include, but are not limited to, $Tb_2O_3$, $Tb_4O_7$, $TbO_2$, $Tb_6O_{11}$, $Dy_2O_3$, $Ho_2O_3$, $Er_2O_3$, $Tm_2O_3$, $Yb_2O_3$, and $Lu_2O_3$.

The rare earth element oxide may also be an oxide of yttrium. By "oxide of yttrium" is meant a compound that contains at least yttrium and oxygen atoms. An example is yttrium oxide (yttria).

In a preferred embodiment of the invention, the rare earth element oxide is yttrium oxide.

It should be noted that the rare earth element oxide may be loaded in the reactor as the oxide, or it may be loaded as an oxide precursor that is oxidized within the reactor.

Examples of oxide precursors include, for instance, rare earth element nitrates, acetates, alkanoates, alkoxides, fluorides, chlorides, bromides, iodides, carbonates, hydroxide, or oxalates. Formation of the oxide within the reactor typically involves heating the precursor at elevated temperature until oxidation of the precursor has occurred. For instance, heating at 400 to 600° C. for 50 to 100 hours is generally sufficient to form the oxide.

The rare earth element oxide may optionally contain a binder and/or matrix material that is different from the oxide of the rare earth element. Non-limiting examples of binders that are useful alone or in combination include various types of hydrated alumina, silicas and/or other inorganic oxide sols, and carbon. Upon heating, the inorganic oxide sol, preferably having a low viscosity, is converted into an inorganic oxide binder component.

Where the rare earth element oxide contains a matrix material, this is preferably different from the rare earth element oxide and any binder. Non-limiting examples of matrix materials include clays or clay-type compositions.

The rare earth element oxide, including any binder or matrix materials, may be unsupported or supported. Non-limiting examples of suitable support materials include titania, alumina, zirconia, silica, carbons, zeolites, magnesium oxide, and mixtures thereof. Where the rare earth element oxide contains a binder, matrix or support material, the amount rare earth element oxide (the active component of the catalyst) may be between 1 and 99 percent by weight based on the total weight of the catalyst (including the oxide, and any support, binder or matrix materials).

The rare earth element oxide may be formed into various shapes and sizes for ease of handling. For instance, the rare earth element oxide (plus any binder, matrix, or support) may be in the form of pellets, spheres, or other shapes commonly used in the industry.

According to the invention, the rare earth element oxide in the reactor is contacted with a halogen source such that it undergoes a halogenation reaction. Halogen sources suitable for use in the invention include any materials capable of providing a reactive halogen atom, e.g., chlorine or fluorine, with chlorine atoms being preferred, to the rare earth element oxide. The halogen source may be a solid, liquid or gas, but preferably it is a gas when contacted with the oxide. The gaseous state may be achieved, for instance, by using a halogen source that is already gaseous at room temperature and pressure, or by vaporizing an otherwise non-gaseous material at the appropriate temperature and/or pressure. Examples of halogen sources include, without limitation, monochloroethane, ammonium chloride, hydrogen chloride, ammonium fluoride, carbon tetrachloride, methyl chloride, methylene chloride, chloroform, chlorine gas, dichloroethane, trichloroethane, tetrachloroethane, other higher halogenated organics, etc.

Typically, the halogenation is conducted by contacting the oxide with the halogen source. Such contacting may be carried out, for instance, at temperatures ranging from room temperature to 650° C. For some halogenating sources, such as monochloroethane, elevated temperature is preferred. By way of more specific example, a bulk yttrium oxide catalyst precursor, for instance, may be converted into an active catalyst by flowing monochloroethane at 50 standard cubic centimeters per minute (sccm) over 5 grams of yttrium oxide at 300° C. for 14 min followed by a thermal treatment in a flowing nitrogen/air mixture (100 sccm nitrogen and 50 sccm air) at 500° C. for four hours.

In some embodiments, halogenation is conducted until the catalyst comprises, in addition to the rare earth element and oxygen, halogen (e.g., chlorine) in an amount of at least 0.001 weight percent, alternatively at least 0.1 weight percent, alternatively at least 1 weight percent, or alternatively at least 2 weight percent. In some embodiments, the activated catalyst may comprise halogen (e.g., chlorine) in an amount of less than 50 weight percent, alternatively 40 weight percent or less, alternatively 30 weight percent or less, alternatively 20 weight percent or less, alternatively 10 weight percent or less, or alternatively 2 weight percent or less.

In some embodiments of the invention, the activated catalyst may be subjected to a calcination step by heating at elevated temperature. Such calcination has been found to render the catalyst even more active and/or selective. In some embodiments, calcination is carried out by heating the material at a temperature of 200° C. or greater, alternatively 400° C. or greater, alternatively 450° C. or greater, or alternatively 500° C. or greater. While there is no specific upper limit on the calcination temperature, the material should be calcined at a temperature below the temperature at which the halide decomposes back to the oxide. Such heating may be continued, for instance, for 30 minutes to 1 hour or more. In some embodiments, it is desirable to purge the reactor with inert gas to remove oxygen before continuing to the alcohol dehydration step.

Following activation of the catalyst (that is, halogenation of the rare earth element oxide) in a vessel, the activated catalyst is used to dehydrate a material to form diaryl ether compound in the same vessel.

According to the process of the invention, an aromatic alcohol compound is dehydrated over the activated catalyst in order to form a diaryl ether compound. Suitable aromatic alcohol compounds include aromatic compounds containing at least one alcohol group and one, two, three or more aromatic moieties. Examples of compounds include phenols and α- and β-hydroxy-substituted fused aromatic ring systems. Apart from the hydroxy substituent, the compounds may be unsubstituted, as in phenol or naphthol. Optionally, however, the compounds may be further substituted with at least one alkyl group containing from 1 to about 10 carbon atoms, preferably, from 1 to 3 carbon atoms, or substituted with at least one alternative substituent which is inert to the dehydration coupling reaction. Suitable inert substituents include cyano, amino, nitro, carboxylic acid (e.g., $C_0$-$C_6$—COOH), ester, $C_6$-$C_{12}$ aryl, $C_2$-$C_6$ alkenyl, alkyloxy, aryloxy, and phenoxy moieties. It is also possible for the aromatic alcohol compound to be substituted with both an alkyl substituent and one of the alternative inert substituents. Each of the aforementioned alkyl substituents and/or alternative inert substituents is attached preferably to an aromatic ring carbon atom which is located in an ortho, meta or para position relative to the hydroxy moiety. Optionally, the alkyl substituent may contain from 3 to 4 carbon atoms, and in combination with a phenol or fused aromatic ring system may form a saturated ring fused to the aromatic ring. An acceptable feed may contain a mixture of aromatic alcohols, including mixtures of the foregoing.

Non-limiting examples of suitable phenols include unsubstituted phenol, m-cresol, p-cresol, 3,4-xylenol, 3,5-xylenol, and 3,4,5-trimethylphenol. Other suitable phenols include compounds corresponding to the above-mentioned examples except that one or more of the methyl substituents are replaced by an ethyl, propyl or butyl substituent. Non-limiting examples of α- and β-hydroxy-substituted fused aromatic ring systems include α- and β-naphthol and 5-tetralinol. Other non-limiting examples of aromatic alcohols include benzenediols (catechol, resorcinol or hydroquinone), o-cresol, o-phenylphenol, m-phenylphenol or p-phenylphenol. One skilled in the art may find other phenols and α- and β-hydroxy-substituted fused aromatic ring systems which are also suitable for the purposes of this invention. Preferably, the aromatic alcohol is unsubstituted phenol or a substituted phenol wherein the substituent is methyl, ethyl or hydroxyl. More preferably, the aromatic alcohol is unsubstituted phenol, cresol or a benzenediol. Most preferably, the aromatic alcohol is unsubstituted phenol.

According to the method of the invention for preparing a diaryl ether, a catalyst as described herein is contacted with the aromatic alcohol compound. The contacting of the catalyst with the aromatic alcohol compound is carried out under reaction conditions such that the diaryl ether is formed.

The catalyst is contacted with the aromatic alcohol compound either in the gas phase or in the liquid phase. In addition, the aromatic alcohol may be diluted with a diluent or it may be neat. Suitable diluents include, without limitation, nitrogen, argon, water vapor, water, oxygen or hydrogen. When a diluent is used, the concentration of the aromatic alcohol compound may be, for instance, 1 volume percent or greater and less than 100 volume percent.

In a preferred embodiment, the aromatic alcohol is contacted with the catalyst in the gas phase. Typically, the aromatic alcohol is introduced into a reactor containing the catalyst at elevated temperature, for instance, between 200 and 800° C., alternatively between 300 and 600° C., alternatively between 400 and 600° C., or alternatively between 450 and 550° C. The reaction may be conducted at atmospheric pressure, under reduced pressure, or at elevated pressure such as up to 5000 psi. In some embodiments, atmospheric pressure or slightly above (e.g., up to about 50 psi) is preferred. In some embodiments, the gas flow rate of the aromatic alcohol over the catalyst (weight hourly space velocity or WHSV) is from 0.01 to 100 grams per gram of catalyst per hour (g/g·h). In some embodiments, WHSV is from 0.1 to 20 g/g·h, alternatively 0.1 to 5 g/g·h, or alternatively 0.1 to 1 g/g·h.

In some embodiments, it may be useful to subject the reactor to startup conditions which may provide various benefits, such as prolonging catalyst life. Suitable startup conditions include, for example, exposing the catalyst to dilute amounts of the aromatic alcohol at lower temperature before changing to full operating conditions as described above and demonstrated by the examples.

Following the reaction, the diaryl ether product is recovered from the catalyst and optionally further purified. Unreacted alcohol and other reaction by-products may be separated using methods known in the art. Such methods include but are not limited to distillation, crystal refining, simulated moving bed technique or a combination thereof.

In some embodiments, the diaryl ether prepared by the process of the invention is diphenyl oxide (DPO). Other diaryl ether compounds that may be prepared by the process of the invention include, without limitation, compounds containing at least one ether functionality whereby two aryl moieties are connected by an oxygen atom (Ar—O—Ar'), including polyaryl compounds and compounds prepared from the aromatic alcohols described above. Specific examples include, but are not limited to, phenoxytoluene isomers, including 3-phenoxytoluene, ditolyl ether isomers, polyphenyl ethers (PPEs), biphenylphenyl ether isomers and naphthyl phenyl ethers.

The diaryl ethers prepared by the invention are useful in a variety of applications, including as high temperature solvents, as intermediates in preparing flame retardants and surfactants, and as components in heat transfer fluids. Furthermore, certain diaryl ethers prepared by the invention are useful as high performance lubricants and as intermediates in preparing pyrethroid insecticides.

In some embodiments, a preferred use of the diaryl ether is in high temperature heat transfer fluids. High temperature heat transfer fluids may be prepared by making the diaryl ether according to the process described above and then mixing the diaryl ether with biphenyl. The amounts necessary to provide a suitable fluid can be readily determined by a person with ordinary skill in the art. For diphenyl oxide and biphenyl, the amount of DPO may be, for instance, from 70 to 75 weight percent based on the total weight of the DPO and biphenyl. A preferred amount of DPO is that required to form a eutectic mixture with the biphenyl, which is about 73.5 weight percent based on the total weight of the DPO and biphenyl.

Some embodiments of the invention will now be described in detail in the following Examples.

EXAMPLES

Example 1

Preparation of the bulk yttrium oxide catalyst precursor, $Y_2O_3$. A solution of yttrium nitrate is made by dissolving 80.1 g $Y(NO_3)_3 \cdot 4H_2O$ in 800 mL deionized $H_2O$ into a four-liter beaker with an overhead stirrer running at 400 rpm. A white precipitate forms as the pH of the solution is adjusted to 9.0 by adding ammonium hydroxide solution with a concentration of 14.6 mol $NH_3$/liter. The slurry is transferred to a one-liter sealed container and heated at 100° C. for 70 hours. The slurry solution is cooled to room temperature and filtered using vacuum filtration in a Buchner funnel. The solid is dispersed in one liter of $H_2O$, filtered, dispersed in a second liter of $H_2O$, and filtered again. The solid is then dried at 110° C. for eighteen hours, then the temperature is increased to 600° C. at a rate of 5° C./min held for four hours, and allowed to cool to room temperature.

The bulk yttrium oxide catalyst is used in the dehydration of phenol after activation with monochloroethane. The yttrium oxide powder is pressed and sieved to obtain particles that are between 0.60 mm and 0.85 mm in diameter. 5.0 grams of particles are loaded into an electrically heated stainless steel reactor tube and heated to the 300° C. in flowing nitrogen. The flowing gas is then changed to 50 mL/min of monochloroethane for 14 minutes and then back to nitrogen flow to purge out the monochloroethane gas. The temperature is then increased to 500° C. and treated with a mixture of 50 mL/min dry air and 100 ml/min nitrogen for four hours. After purging the reactor with nitrogen, vapor-phase phenol is passed through the reactor tube. The conversion of phenol is carried out at a weight hourly space velocity of 0.2 (WHSV=gram phenol/gram catalyst·hour) and at 500° C. in the same vessel as the halogenation of the yttrium oxide. Results are shown in Table 1 for two different sets of test conditions for the dehydration of the phenol.

spectroscopy (XRF) to 17.23 wt. % chlorine, 69.63 wt. % lanthanum and 13.14 wt. % oxygen (balance). Thus, the elemental composition of the catalyst is $La_{1.00}O_{1.64}Cl_{0.97}$. The specific surface area (BET) of the catalyst sample is measured to 6.2 $m^2/g$ and its pore volume to 0.013 $cm^3/g$. The XRD data shows the presence of lanthanum oxychloride phases.

The lanthanum oxychloride catalyst is used for the dehydration of phenol. The powder is pressed and sieved to obtain particles that are between 0.60 mm and 0.85 mm in diameter. The particles are loaded into an electrically heated stainless steel reactor tube and heated to the reaction temperature with nitrogen flowing through the tube. After the reaction temperature is reached, vapor-phase phenol is passed through the reactor tube. The conversion of phenol is

TABLE 1

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C.<br>Feed: PhOH<br>ToS = 2.55 hrs<br>WHSV 0.2 hr$^{-1}$ | 26.12% | 93.78% | 0.42% | 5.24% | 0.05% | 0.40% | 0.11% |
| T = 500° C.<br>Feed: PhOH<br>ToS = 11.25 hrs<br>WHSV 0.2 hr$^{-1}$ | 23.20% | 94.02% | 0.51% | 5.21% | 0.11% | 0.07% | 0.07% |

Example 2

The synthesis of lanthanum oxychloride is carried out by thermal decomposition of $LaCl_3.7H_2O$. A sample of the powdered precursor (approximately 10 g) is calcined in air in a static calcination oven under the following temperature protocol: ramp 1.41° C./min to 550° C., dwell 3 hrs at 550° C., cool down to room temperature. The elemental composition of the catalyst is assayed by X-ray fluorescence carried out at a weight hourly space velocity of 1 (WHSV=gram phenol/gram catalyst-hour) and at 500° C. Test conditions and results are shown in Table 2.

Similar results are expected if lanthanum oxide was halogenated to lanthanum oxychloride in the same vessel as the dehydration reaction using a chlorination process as illustrated in Example 1.

TABLE 2

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C.<br>Feed: PhOH<br>ToS = 1.5 hrs<br>WHSV 1 hr$^{-1}$ | 0.70% | 95.86% | 0.02% | 4.12% | 0.00% | 0.00% | 0.00% |
| T = 500° C.<br>Feed: PhOH<br>ToS = 2.75 hrs<br>WHSV 1 hr$^{-1}$ | 0.82% | 95.83% | 0.07% | 4.09% | 0.00% | 0.00% | 0.00% |
| T = 500° C.<br>Feed: PhOH<br>ToS = 3.75 hrs<br>WHSV 1 hr$^{-1}$ | 0.82% | 95.90% | 0.18% | 3.93% | 0.00% | 0.00% | 0.00% |
| T = 500° C.<br>Feed: PhOH<br>ToS = 7.5 hrs<br>WHSV 1 hr$^{-1}$ | 0.74% | 95.70% | 0.13% | 4.17% | 0.00% | 0.00% | 0.00% |

OPP: orthophenylphenol.
DBF: dibenzofuran.
O-BIPPE: ortho-biphenylphenyl ether.
M-BIPPE: meta-biphenylphenyl ether.
P-BIPPE: para-biphenylphenyl ether.
PhOH: phenol.
N2: nitrogen.
ToS: time on stream (ToS = 0 hours defined at start of phenol flow).

Example 3

A 1M $PrCl_3$ solution, prepared by dissolving 10 g $PrCl_3$ in 50 mL DI $H_2O$, is added dropwise along with tetrapropylammonium hydroxide (76.36 g) over 15 min into a 600 mL beaker containing an initial 100 mL DI $H_2O$. The solution is stirred at 500 rpm on magnetic stir plate with a 4.5 inch stir bar. The resulting green precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield approximately 8 g of metal oxychloride product. Neutron activation analysis reveals a total chlorine concentration of 1.17 wt %.

The catalyst is evaluated using a similar procedure as in Example 2. Test conditions and results are shown in Table 3. Similar results are expected if praseodymium oxide was halogenated to praseodymium oxychloride in the same vessel as the dehydration reaction using a chlorination process as illustrated in Example 1.

TABLE 3

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1 hr WHSV 1 hr$^{-1}$ | 2.63% | 73.15% | 1.94% | 24.91% | 0.00% | 0.00% | 0.00% |
| T = 500° C. Feed: PhOH ToS = 2 hrs WHSV 1 hr$^{-1}$ | 2.75% | 78.64% | 2.16% | 19.20% | 0.00% | 0.00% | 0.00% |
| T = 500° C. Feed: PhOH ToS = 3.5 hrs WHSV 1 hr$^{-1}$ | 3.70% | 76.14% | 1.92% | 21.94% | 0.00% | 0.00% | 0.00% |
| T = 500° C. Feed: PhOH ToS = 5.75 hrs WHSV 1 hr$^{-1}$ | 2.28% | 73.28% | 3.58% | 23.14% | 0.00% | 0.00% | 0.00% |

Example 4

A 1M $NdCl_3$ solution, prepared by dissolving 17.94 g $NdCl_3$ in 50 mL DI $H_2O$, is added dropwise along with tetrapropylammonium hydroxide (76.26 g, from a 40 wt % TPAOH solution) over 15 min into a 600 mL beaker containing an initial 100 mL DI $H_2O$. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield approximately 8 g of metal oxychloride product. Neutron activation analysis reveals a total chlorine concentration of 5.8 wt %.

The catalyst is evaluated using a similar procedure as in Example 2. Test conditions and results are shown in Table 4. Similar results are expected if neodymium oxide was halogenated to neodymium oxychloride in the same vessel as the dehydration reaction using a chlorination process as illustrated in Example 1.

TABLE 4

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.75 hrs WHSV 1 hr$^{-1}$ | 1.32% | 37.89% | 3.84% | 56.56% | 0.00% | 0.21% | 1.50% |
| T = 500° C. Feed: PhOH ToS = 2.75 hrs WHSV 1 hr$^{-1}$ | 0.71% | 37.84% | 5.95% | 51.32% | 0.00% | 0.38% | 4.51% |

TABLE 4-continued

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C.<br>Feed: PhOH<br>ToS = 4 hrs<br>WHSV 1 hr$^{-1}$ | 0.71% | 52.64% | 6.67% | 40.37% | 0.00% | 0.00% | 0.32% |

Example 5

A 1M SmCl$_3$ solution, prepared by dissolving 18.254 g SmCl$_3$ in 50 ml DI H$_2$O, is added dropwise along with tetrapropylammonium hydroxide (76.288 g, from a 40 wt % TPAOH solution) over 15 min into a 600 ml beaker containing an initial 100 ml DI H$_2$O. The solution is stirred at 500 rpm on a magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield the solid metal oxychloride product.

The catalyst is evaluated using a similar procedure as in Example 2. Test conditions and results are shown in Table 5. Similar results are expected if samarium oxide was halogenated to samarium oxychloride in the same vessel as the dehydration reaction using a chlorination process as illustrated in Example 1.

TABLE 5

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C.<br>Feed: PhOH<br>ToS = 1.75 h<br>WHSV 1 h$^{-1}$ | 6.08% | 92.99% | 0.02% | 6.99% | 0.00% | 0.00% | 0.00% |
| T = 500° C.<br>Feed: PhOH<br>ToS = 2.75 h<br>WHSV 1 h$^{-1}$ | 5.36% | 92.16% | 0.90% | 6.93% | 0.00% | 0.00% | 0.00% |
| T = 500° C.<br>Feed: PhOH<br>ToS = 5 h<br>WHSV 1 h$^{-1}$ | 5.16% | 91.91% | 1.49% | 6.60% | 0.00% | 0.00% | 0.00% |
| T = 500° C.<br>Feed: PhOH<br>ToS = 7 h<br>WHSV 1 h$^{-1}$ | 4.91% | 92.72% | 0.03% | 7.24% | 0.00% | 0.00% | 0.00% |

Example 6

A 1M GdCl$_3$ solution, prepared by dissolving 18.633 g GdCl$_3$ in 50 ml DI H$_2$O, is added dropwise along with tetrapropylammonium hydroxide (76.261 g, from a 40 wt % TPAOH solution) over 15 min into a 600 ml beaker containing an initial 100 ml DI H$_2$O. The solution is stirred at 500 rpm on a magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield the solid metal oxychloride product.

The catalyst is evaluated using a similar procedure as in Example 2. Test conditions and results are shown in Table 6. Similar results are expected if gadolinium oxide was halogenated to gadolinium oxychloride in the same vessel as the dehydration reaction using a chlorination process as illustrated in Example 1.

TABLE 6

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C.<br>Feed: PhOH<br>ToS = 1 h<br>WHSV 1 h$^{-1}$ | 16.53% | 92.44% | 0.03% | 6.96% | 0.13% | 0.25% | 0.19% |
| T = 500° C.<br>Feed: PhOH | 11.05% | 94.78% | 0.50% | 4.21% | 0.11% | 0.20% | 0.21% |

TABLE 6-continued

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| ToS = 2.75 h WHSV 1 h⁻¹ | | | | | | | |
| T = 500° C. Feed: PhOH ToS = 3.5 h WHSV 1 h⁻¹ | 9.44% | 94.64% | 0.82% | 3.85% | 0.13% | 0.17% | 0.38% |
| T = 500° C. Feed: PhOH ToS = 4.75 h WHSV 1 h⁻¹ | 7.09% | 96.00% | 0.22% | 3.36% | 0.04% | 0.11% | 0.26% |

Example 7

The synthesis of chlorinated holmium oxide (Cl—$Ho_2O_3$) is carried out by a thermal decomposition of $HoCl_3 \cdot 6H_2O$. Thus, a sample of the powdered precursor (approximately 10 g) is calcined in air in a static calcination oven under the following temperature protocol: ramp 1.41° C./min to 550° C., dwell 3 hours at 550° C., cool down to room temperature. The chlorine content of the catalyst is assayed by XRF to 13.58 wt. % chlorine. The XRD data shows the presence of holmium oxychloride phases.

The catalyst is used in the dehydration of phenol using a similar procedure as in Example 2. Test conditions and results are shown in Table 7. Similar results are expected if holmium oxide was halogenated to holmium oxychloride in the same vessel as the dehydration reaction using a chlorination process as illustrated in Example 1.

TABLE 7

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 2.25 hrs WHSV 1 hr⁻¹ | 1.23% | 92.68% | 0.31% | 7.01% | 0.00% | 0.00% | 0.00% |
| T = 500° C. Feed: PhOH ToS = 3.25 hrs WHSV 1 hr⁻¹ | 1.36% | 91.33% | 0.31% | 8.37% | 0.00% | 0.00% | 0.00% |
| T = 500° C. Feed: PhOH ToS = 4.25 hrs WHSV 1 hr⁻¹ | 1.57% | 88.91% | 0.17% | 10.91% | 0.00% | 0.00% | 0.00% |
| T = 500° C. Feed: PhOH ToS = 5.5 hrs WHSV 1 hr⁻¹ | 1.45% | 87.46% | 0.40% | 12.14% | 0.00% | 0.00% | 0.00% |

Example 8

A 1M $DyCl_3$ solution, prepared by dissolving 18.849 g $DyCl_3$ in 50 mL DI $H_2O$, is added dropwise along with tetrapropylammonium hydroxide (76.261 g, from a 40 wt % TPAOH solution) over 15 min into a 600 mL beaker containing an initial 100 mL DI $H_2O$. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 8.6 g of metal oxychloride product.

The catalyst is evaluated using a similar procedure as in Example 2. Test conditions and results are shown in Table 8. Similar results are expected if dysprosium oxide was halogenated to dysprosium oxychloride in the same vessel as the dehydration reaction using a chlorination process as illustrated in Example 1.

TABLE 8

|  | Conversion | Selectivity [mol. %] | | | | | |
|---|---|---|---|---|---|---|---|
| Test Conditions | [mol. %] Phenol | Diphenyl Oxide | OPP | DBF | O-BIPPE | M-BIPPE | P-BIPPE |
| T = 500° C. Feed: PhOH ToS = 1.25 hrs WHSV 1 hr⁻¹ | 8.30% | 96.11% | 0.01% | 3.61% | 0.00% | 0.14% | 0.14% |
| T = 500° C. Feed: PhOH ToS = 2.25 hrs WHSV 1 hr⁻¹ | 11.74% | 97.58% | 0.10% | 2.14% | 0.00% | 0.08% | 0.09% |
| T = 500° C. Feed: PhOH ToS = 3.75 hrs WHSV 1 hr⁻¹ | 6.36% | 96.68% | 0.25% | 2.79% | 0.00% | 0.11% | 0.16% |
| T = 500° C. Feed: PhOH ToS = 4.75 hrs WHSV 1 hr⁻¹ | 11.88% | 95.96% | 0.10% | 3.63% | 0.04% | 0.09% | 0.19% |

Example 9

A 1M $YbCl_3$ solution, prepared by dissolving 19.387 g $YbCl_3$ in 50 mL DI $H_2O$, is added dropwise along with tetrapropylammonium hydroxide (76.265 g, from a 40 wt % TPAOH solution) over 15 min into a 600 mL beaker containing an initial 100 mL DI $H_2O$. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 9 g of metal oxychloride product.

The catalyst is evaluated using a similar procedure as in Example 2. Test conditions and results are shown in Table 9. Similar results are expected if yttrium oxide was halogenated to yttrium oxychloride in the same vessel as the dehydration reaction using a chlorination process as illustrated in Example 1.

TABLE 9

|  | Conversion | Selectivity [mol. %] | | | | | |
|---|---|---|---|---|---|---|---|
| Test Conditions | [mol. %] Phenol | Diphenyl Oxide | OPP | DBF | O-BIPPE | M-BIPPE | P-BIPPE |
| T = 500° C. Feed: PhOH ToS = 1.5 hrs WHSV 1 hr⁻¹ | 19.76% | 97.39% | 0.15% | 2.18% | 0.02% | 0.19% | 0.07% |
| T = 500° C. Feed: PhOH ToS = 2.5 hrs WHSV 1 hr⁻¹ | 22.20% | 97.53% | 0.06% | 2.20% | 0.02% | 0.14% | 0.06% |
| T = 500° C. Feed: PhOH ToS = 3 hrs WHSV 1 hr⁻¹ | 22.29% | 97.55% | 0.10% | 2.10% | 0.04% | 0.14% | 0.06% |

Example 10

A 1M $ErCl_3$ solution, prepared by dissolving 15.272 g $ErCl_3$ in 40 mL DI $H_2O$, is added dropwise along with tetrapropylammonium hydroxide (61.030 g, from a 40 wt % TPAOH solution) over 15 min into a 600 mL beaker containing an initial 100 mL DI $H_2O$. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 7.4 g of metal oxychloride product.

The catalyst is evaluated using a similar procedure as in Example 2. Test conditions and results are shown in Table 10. Similar results are expected if erbium oxide was halogenated to erbium oxychloride in the same vessel as the dehydration reaction using a chlorination process as illustrated in Example 1.

TABLE 10

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 4.5 hrs WHSV 1 hr$^{-1}$ | 23.67% | 97.71% | 0.14% | 1.99% | 0.02% | 0.10% | 0.04% |
| T = 500° C. Feed: PhOH ToS = 5.5 hrs WHSV 1 hr$^{-1}$ | 22.86% | 97.75% | 0.18% | 1.85% | 0.01% | 0.15% | 0.06% |

Example 11

A 1M HoCl$_3$ solution, prepared by dissolving 11.388 g HoCl$_3$ in 30 mL DI H$_2$O, is added dropwise along with tetrapropylammonium hydroxide (45.759 g, from a 40 wt % TPAOH solution) over 15 min into a 600 mL beaker containing an initial 100 mL DI H$_2$O. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 5 g of metal oxychloride product.

The catalyst is evaluated using a similar procedure as in Example 2. Test conditions and results are shown in Table 11. Similar results are expected if holmium oxide was halogenated to holmium oxychloride in the same vessel as the dehydration reaction using a chlorination process as illustrated in Example 1.

with a concentration of 14.6 mol NH$_3$/liter. The slurry is transferred to a one liter sealed container and heated at 100° C. for 70 hours. The slurry solution is cooled to room temperature and filtered using vacuum filtration in a Buchner funnel. The solid is dispersed in one liter of H$_2$O, filtered, dispersed in a second liter of H$_2$O, and filtered again. The solid is then dried at 110° C. for eighteen hours, then the temperature is increased to 600° C. at a rate of 5° C./min held for four hours, and allowed to cool to room temperature.

Preparation of chloride-activated yttrium oxide using ammonium chloride. A solution of ammonium chloride is made by dissolving 0.0604 g of ammonium chloride in 2.0608 mL deionized H$_2$O. The ammonium chloride solution is then added to 2.0 g of Y$_2$O$_3$ dropwise with constant stirring using a spatula. The sample is then dried in air at 120° C. for four hours and then the temperature is increased

TABLE 11

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.75 hrs WHSV 1 hr$^{-1}$ | 12.22% | 97.77% | 0.21% | 1.87% | 0.02% | 0.07% | 0.07% |
| T = 500° C. Feed: PhOH ToS = 3.75 hrs WHSV 1 hr$^{-1}$ | 12.73% | 97.90% | 0.28% | 1.63% | 0.00% | 0.13% | 0.07% |
| T = 500° C. Feed: PhOH ToS = 5 hrs WHSV 1 hr$^{-1}$ | 12.34% | 97.95% | 0.24% | 1.61% | 0.02% | 0.11% | 0.05% |
| T = 500° C. Feed: PhOH ToS = 7 hrs WHSV 1 hr$^{-1}$ | 12.02% | 97.88% | 0.12% | 1.82% | 0.00% | 0.11% | 0.07% |

Example 12

Preparation of the bulk yttrium oxide catalyst precursor, Y$_2$O$_3$. A solution of yttrium nitrate is made by dissolving 80.1 g Y(NO$_3$)$_3$. 4H$_2$O in 800 mL deionized H$_2$O into a four-liter beaker with an overhead stirrer running at 400 rpm. A white precipitate forms as the pH of the solution is adjusted to 9.0 by adding ammonium hydroxide solution to 400° C. with a ramp rate of 5° C./min and held for four hours.

The catalyst is evaluated using a similar procedure as in Example 2. Test conditions and results are shown in Table 12. Similar results are expected if yttrium oxide was halogenated to yttrium oxychloride in the same vessel as the dehydration reaction using a chlorination process as illustrated in Example 1.

TABLE 12

| Test Conditions | Conversion [mol. %] Phenol | Selectivity [mol. %] | | | | |
|---|---|---|---|---|---|---|
| | | Diphenyl Oxide | OPP | DBF | O-BIPPE | M-BIPPE | P-BIPPE |
| T = 500° C.<br>Feed: PhOH<br>ToS = 1.25 hrs<br>WHSV 1 hr$^{-1}$ | 11.62% | 96.91% | 0.09% | 3.00% | 0.00% | 0.00% | 0.00% |
| T = 500° C.<br>Feed: PhOH<br>ToS = 2 hrs<br>WHSV 1 hr$^{-1}$ | 6.53% | 96.88% | 0.06% | 3.06% | 0.00% | 0.00% | 0.00% |
| T = 500° C.<br>Feed: PhOH<br>ToS = 3 hrs<br>WHSV 1 hr$^{-1}$ | 4.16% | 96.63% | 0.13% | 3.24% | 0.00% | 0.00% | 0.00% |
| T = 500° C.<br>Feed: PhOH<br>ToS = 4 hrs<br>WHSV 1 hr$^{-1}$ | 5.48% | 96.34% | 0.24% | 3.42% | 0.00% | 0.00% | 0.00% |

Example 13

Preparation of chloride-activated yttrium oxide using aqueous hydrogen chloride. A solution of hydrogen chloride is made by mixing 0.0983 mL HCl (10 mol/L) with 1.9617 mL deionized H$_2$O. The hydrogen chloride solution is then added to 2.0 g of bulk yttrium oxide precursor prepared using the method from Example 13 dropwise with constant stirring using a spatula. The sample is then dried in air at 120° C. for four hours and then temperature is increased to 400° C. with a ramp rate of 5° C./min and held for four hours.

The catalyst is evaluated using a similar procedure as in Example 2. Test conditions and results are shown in Table 13. Similar results are expected if yttrium oxide was halogenated to yttrium oxychloride in the same vessel as the dehydration reaction using a chlorination process as illustrated in Example 1.

Example 14

Preparation of chloride-activated yttrium oxide using aqueous hydrogen chloride. A solution of hydrogen chloride is made by mixing 0.1958 mL HCl (10 mol/L) with 1.8642 mL deionized H$_2$O. The hydrogen chloride solution is then added to 2.0 g of bulk yttrium oxide precursor prepared using the method from Example 13 dropwise with constant stirring using a spatula. The sample is then dried in air at 120° C. for four hours and then temperature is increased to 400° C. with a ramp rate of 5° C./min and held for four hours.

The catalyst is evaluated using a similar procedure as in Example 2. Test conditions and results are shown in Table 14. Similar results are expected if yttrium oxide was halogenated to yttrium oxychloride in the same vessel as the dehydration reaction using a chlorination process as illustrated in Example 1.

TABLE 13

| Test Conditions | Conversion [mol. %] Phenol | Selectivity [mol. %] | | | | |
|---|---|---|---|---|---|---|
| | | Diphenyl Oxide | OPP | DBF | O-BIPPE | M-BIPPE | P-BIPPE |
| T = 500° C.<br>Feed: PhOH<br>ToS = 1.25 hrs<br>WHSV 1 hr$^{-1}$ | 2.83% | 95.03% | 0.02% | 4.95% | 0.00% | 0.00% | 0.00% |
| T = 500° C.<br>Feed: PhOH<br>ToS = 2.5 hrs<br>WHSV 1 hr$^{-1}$ | 2.41% | 96.48% | 0.02% | 3.51% | 0.00% | 0.00% | 0.00% |
| T = 500° C.<br>Feed: PhOH<br>ToS = 3.5 hrs<br>WHSV 1 hr$^{-1}$ | 2.71% | 94.46% | 0.06% | 5.48% | 0.00% | 0.00% | 0.00% |
| T = 500° C.<br>Feed: PhOH<br>ToS = 4.25 hrs<br>WHSV 1 hr$^{-1}$ | 2.32% | 95.45% | 0.02% | 4.54% | 0.00% | 0.00% | 0.00% |

TABLE 14

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.5 hrs WHSV 1 hr$^{-1}$ | 7.11% | 94.93% | 0.00% | 4.96% | 0.00% | 0.00% | 0.11% |
| T = 500° C. Feed: PhOH ToS = 2.5 hrs WHSV 1 hr$^{-1}$ | 19.67% | 95.02% | 0.17% | 4.64% | 0.06% | 0.06% | 0.05% |
| T = 500° C. Feed: PhOH ToS = 3.25 hrs WHSV 1 hr$^{-1}$ | 13.00% | 96.99% | 0.07% | 2.71% | 0.03% | 0.13% | 0.06% |
| T = 500° C. Feed: PhOH ToS = 4.25 hrs WHSV 1 hr$^{-1}$ | 6.73% | 96.47% | 0.03% | 2.61% | 0.00% | 0.08% | 0.81% |

Example 15

Preparation of chloride-activated yttrium oxide using aqueous hydrogen chloride. A solution of hydrogen chloride is made by mixing 0.4703 mL HCl (10 mol/L) with 1.6681 mL deionized H$_2$O. The hydrogen chloride solution is then added to 2.0 g of bulk yttrium oxide precursor prepared using the method from Example 13 dropwise with constant stirring using a spatula. The sample is then dried in air at 120° C. for four hours and then temperature is increased to 400° C. with a ramp rate of 5° C./min and held for four hours.

The catalyst is evaluated using a similar procedure as in Example 2. Test conditions and results are shown in Table 15. Similar results are expected if yttrium oxide was halogenated to yttrium oxychloride in the same vessel as the dehydration reaction using a chlorination process as illustrated in Example 1.

Example 16

Preparation of chloride-activated yttrium oxide using aqueous hydrogen chloride. A solution of hydrogen chloride is made by mixing 0.9406 mL HCl (10 mol/L) with 1.2762 mL deionized H$_2$O. The hydrogen chloride solution is then added to 2.0 g of bulk yttrium oxide precursor prepared using the method from Example 13 dropwise with constant stirring using a spatula. The sample is then dried in air at 120° C. for four hours and then temperature is increased to 400° C. with a ramp rate of 5° C./min and held for four hours.

The catalyst is evaluated using a similar procedure as in Example 2. Test conditions and results are shown in Table 16. Similar results are expected if yttrium oxide was halogenated to yttrium oxychloride in the same vessel as the dehydration reaction using a chlorination process as illustrated in Example 1

TABLE 15

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.5 hrs WHSV 1 hr$^{-1}$ | 7.35% | 97.13% | 0.08% | 2.57% | 0.00% | 0.04% | 0.18% |
| T = 500° C. Feed: PhOH ToS = 2.5 hrs WHSV 1 hr$^{-1}$ | 8.93% | 97.18% | 0.14% | 2.67% | 0.00% | 0.00% | 0.00% |
| T = 500° C. Feed: PhOH ToS = 3.25 hrs WHSV 1 hr$^{-1}$ | 7.58% | 97.19% | 0.02% | 2.65% | 0.00% | 0.10% | 0.04% |
| T = 500° C. Feed: PhOH ToS = 4.25 hrs WHSV 1 hr$^{-1}$ | 8.05% | 97.34% | 0.09% | 2.48% | 0.00% | 0.00% | 0.09% |

TABLE 16

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 2.5 hrs WHSV 1 hr$^{-1}$ | 1.44% | 98.95% | 0.00% | 1.05% | 0.00% | 0.00% | 0.00% |
| T = 500° C. Feed: PhOH ToS = 4 hrs WHSV 1 hr$^{-1}$ | 1.77% | 98.64% | 0.00% | 1.36% | 0.00% | 0.00% | 0.00% |
| T = 500° C. Feed: PhOH ToS = 5.75 hrs WHSV 1 hr$^{-1}$ | 1.90% | 98.60% | 0.01% | 1.39% | 0.00% | 0.00% | 0.00% |
| T = 500° C. Feed: PhOH ToS = 7 hrs WHSV 1 hr$^{-1}$ | 2.08% | 98.39% | 0.00% | 1.61% | 0.00% | 0.00% | 0.00% |

Example 17

Preparation of zirconia-supported yttrium oxide precursor. A solution of zirconyl chloride is made by dissolving 161.05 g ZrOCl$_2$ in 2 L deionized H$_2$O. Solution is added over 1 hour into a 4 L beaker with an overhead stirrer running at 400 rpm starting with 500 ml deionized H$_2$O. Ammonium hydroxide solution with a concentration of 14.6 mol NH$_3$/liter is added as needed to maintain a pH of 10.0 in the solution. A white precipitate is formed and is separated from the liquid by centrifugation for 45 minutes at 3000 rpm and decanting the liquid. The solids are then redispersed in one liter of 60° C. deionized H$_2$O and the pH is adjusted to 10.0 using ammonium hydroxide. The solids are then separated again by centrifugation and the washing process is repeated four times. The zirconium oxyhydroxide solids are then dried at 120° C. for eighteen hours. A solution of yttrium nitrate is made by dissolving 0.8443 g of yttrium nitrate to enough water to make a solution that is 1.3 mL. The yttrium nitrate solution is then added dropwise with constant stirring using a spatula to 5.0 g of zirconium oxyhydroxide produced in the previous step. The sample is then dried in air at 110° C. for four hours and then the temperature is increased to 600° C. with a ramp rate of 5° C./min and held for four hours.

Preparation of chloride-activated yttrium oxide using aqueous hydrogen chloride. A solution of hydrogen chloride is made by mixing 0.294 mL HCl (10 mol/L) with 0.126 mL deionized H$_2$O. The hydrogen chloride solution is then added dropwise with constant stirring using a spatula to 3.0 g of zirconia-supported yttrium oxide precursor prepared using the method above. The sample is then dried in air at 120° C. for four hours and then temperature is increased to 400° C. with a ramp rate of 5° C./min and held for four hours.

The catalyst is evaluated using a similar procedure as in Example 2. Test conditions and results are shown in Table 17. Similar results are expected if zirconia oxide was halogenated to zirconia oxychloride in the same vessel as the dehydration reaction using a chlorination process as illustrated in Example 1.

TABLE 17

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.5 hrs WHSV 1 hr$^{-1}$ | 11.35% | 86.62% | 1.26% | 12.04% | 0.00% | 0.08% | 0.00% |
| T = 500° C. Feed: PhOH ToS = 2 hrs WHSV 1 hr$^{-1}$ | 6.63% | 85.43% | 1.18% | 13.29% | 0.00% | 0.00% | 0.10% |
| T = 500° C. Feed: PhOH ToS = 2.75 hrs WHSV 1 hr$^{-1}$ | 7.48% | 83.46% | 0.49% | 15.42% | 0.00% | 0.25% | 0.38% |
| T = 500° C. Feed: PhOH ToS = 3.25 hrs WHSV 1 hr$^{-1}$ | 8.55% | 81.60% | 1.19% | 16.29% | 0.00% | 0.37% | 0.56% |

Example 18

Preparation of fluoride-activated yttrium oxide using ammonium fluoride. A solution of ammonium fluoride is made by dissolving 0.234 g NH$_4$F in 2.859 mL deionized H$_2$O. The ammonium fluoride solution is then added to 3.0 g of bulk yttrium oxide precursor prepared using the method from Example 13 dropwise with constant stirring using a spatula. The sample is then dried in air at 120° C. for four hours and then temperature is increased to 400° C. with a ramp rate of 5° C./min and held for four hours.

The catalyst is evaluated using a similar procedure as in Example 2. Test conditions and results are shown in Table 18. Similar results are expected if yttrium oxide was halogenated to yttrium oxyfluoride in the same vessel as the dehydration reaction in like fashion as illustrated in Example 1.

TABLE 18

| Test Conditions | Conversion [mol. %] Phenol | Selectivity [mol. %] | | | | | |
| --- | --- | --- | --- | --- | --- | --- | --- |
| | | Diphenyl Oxide | OPP | DBF | O-BIPPE | M-BIPPE | P-BIPPE |
| T = 500° C. Feed: PhOH ToS = 2.25 hrs WHSV 1 hr$^{-1}$ | 0.37% | 91.55% | 0.01% | 8.44% | 0.00% | 0.00% | 0.00% |
| T = 500° C. Feed: PhOH ToS = 3.5 hrs WHSV 1 hr$^{-1}$ | 0.23% | 92.55% | 0.02% | 7.43% | 0.00% | 0.00% | 0.00% |
| T = 500° C. Feed: PhOH ToS = 5 hrs WHSV 1 hr$^{-1}$ | 0.32% | 91.81% | 0.18% | 8.01% | 0.00% | 0.00% | 0.00% |
| T = 500° C. Feed: PhOH ToS = 6.5 hrs WHSV 1 hr$^{-1}$ | 0.25% | 91.59% | 0.04% | 8.38% | 0.00% | 0.00% | 0.00% |

What is claimed is:

1. A method for preparing a diaryl ether compound, the method comprising:
   providing a reaction vessel having loaded therein a rare earth element oxide selected from a group consisting of lanthanum oxide, praseodymium oxide, neodymium oxide, samarium oxide, europium oxide, gadolinium oxide, terbium oxide, dysprosium oxide, holmium oxide, erbium oxide, thulium oxide, ytterbium oxide, lutetium oxide and yttrium oxide;
   halogenating the rare earth element oxide with a halogen source to form an activated catalyst containing 0.001 weight-percent or more and less than 50 weight-percent halogen;
   calcining the activated catalyst; and
   dehydrating an aromatic alcohol compound over the activated catalyst to form the diaryl ether compound, where the halogenating and dehydrating steps occur in the same vessel.

2. The method of claim 1 wherein calcination is conducted by heating the activated catalyst at 400° C. or greater.

3. The method of claim 1 wherein the halogen source provides chlorine atoms or fluorine atoms.

4. The method of claim 1 wherein the dehydration of the aromatic alcohol compound is conducted at a temperature from 200 to 800° C.

5. The method of claim 1 wherein the aromatic alcohol compound is diluted with a diluent.

6. The method of claim 1 wherein the aromatic alcohol compound is phenol and the diaryl ether produced is diphenyl oxide.

7. A method for producing a heat transfer fluid, the method comprising:
   (a) preparing a diaryl ether compound by
      (i) providing a reaction vessel having loaded therein a rare earth element oxide selected from a group consisting of lanthanum oxide, praseodymium oxide, neodymium oxide, samarium oxide, europium oxide, gadolinium oxide, terbium oxide, dysprosium oxide, holmium oxide, erbium oxide, thulium oxide, ytterbium oxide, lutetium oxide and yttrium oxide;
      (ii) halogenating the rare earth element oxide with a halogen source to form an activated catalyst containing 0.001 weight-percent or more and less than 50 wt % halogen;
      (iii) calcining the activated catalyst; and
      (iv) dehydrating an aromatic alcohol compound over the activated catalyst to form the diaryl ether compound, where the halogenating and dehydrating steps occur in the same vessel;
   (b) isolating the diaryl ether from the activated catalyst; and
   (c) mixing the isolated diaryl ether compound with biphenyl such that a eutectic mixture is formed.

* * * * *